United States Patent

Kocsis et al.

[11] 4,202,900
[45] May 13, 1980

[54] DERIVATIVES OF PENAM-3-CARBOXYLIC ACID AND A PHARMACEUTICAL COMPOSITION CONTAINING THE SAME

[75] Inventors: Karoly Kocsis, Basel; Bruno Fechtig, Reinach; Hans Bickel, Binningen, all of Switzerland

[73] Assignee: Ciba-Geigy Corporation, Ardsley, N.Y.

[21] Appl. No.: 900,696

[22] Filed: Apr. 28, 1978

Related U.S. Application Data

[60] Continuation of Ser. No. 749,934, Dec. 13, 1976, abandoned, which is a division of Ser. No. 398,512, Sep. 18, 1973, Pat. No. 4,015,000.

[30] Foreign Application Priority Data

Sep. 27, 1972 [CH] Switzerland ............ 14257/72
Mar. 14, 1973 [CH] Switzerland ............ 3694/73
May 24, 1973 [CH] Switzerland ............ 7444/73

[51] Int. Cl.$^2$ ............ A61K 31/43; C07D 499/68
[52] U.S. Cl. ............ 424/251; 260/239.1; 424/246; 424/271
[58] Field of Search ............ 260/239.1; 424/271, 424/246, 251

[56] References Cited

U.S. PATENT DOCUMENTS

| | | | |
|---|---|---|---|
| 3,433,784 | 3/1969 | Long et al. | 260/239.1 |
| 3,953,428 | 4/1976 | Murakami et al. | 260/239.1 |
| 4,008,220 | 2/1977 | Tobiki et al. | 260/239.1 |
| 4,015,000 | 3/1977 | Kocsis et al. | 424/246 |

*Primary Examiner*—Joseph E. Evans
*Assistant Examiner*—Vera C. Clarke
*Attorney, Agent, or Firm*—John J. Maitner

[57] ABSTRACT

6-Acylamino-penam-3-carboxylic acids and 7-acylamino-3-cephem-4-carboxylic acids in which the acyl group has the formula

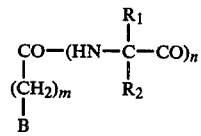

in which $R_1$ is hydrogen, $R_2$ is optionally substituted phenyl, thienyl or furyl or $R_1$ and $R_2$ together are optionally substituted cycloalkyl, n and m independently of one another represent 0 or 1 and B represents an optionally substituted 2,6-dioxo- or 2,6-dithioxo-1,2,3,6-tetrahydro-pyrimidyl, 2-thioxo-6-oxo-1,2,3,6-tetrahydropyrimidyl, 2,6-dihydroxy- or 2,6-dimercapto-pyrimidyl, 2-mercapto-6-hydroxy-pyrimidyl, 2,6-diaminopyrimidyl, 2-amino-6-hydroxy-pyrimidyl or 2,6-dihalogenopyrimidyl radical, these radicals being bonded in the 4- or 5-position.

6 Claims, No Drawings

DERIVATIVES OF PENAM-3-CARBOXYLIC ACID AND A PHARMACEUTICAL COMPOSITION CONTAINING THE SAME

This is a continuation of application Ser. No. 749,934, filed on Dec. 13, 1976, now abandoned, which is a divisional of application Ser. No. 398,512, filed on Sept. 18, 1973, now U.S. Pat. No. 4,015,000, issued on Mar. 29, 1977.

The invention relates to new therapeutically valuable derivatives of 6-amino-2,2-dimethyl-penam-3-carboxylic acid and of 7-amino-ceph-3-em-4-carboxylic acid and their salts, processes for their manufacture and pharmaceutical preparations which contain the new compounds.

The new compounds have the general formula I

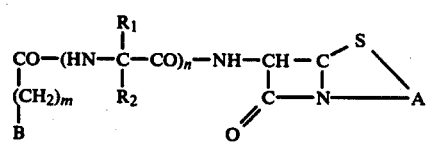

wherein the grouping —S—A— represents a radical of the formula Ia or Ib

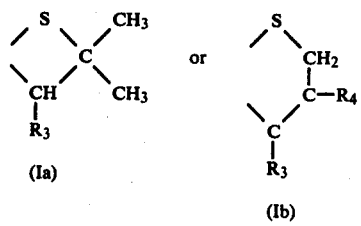

wherein $R_3$ denotes a free or therapeutically usable esterified carboxyl group and $R_4$ represents hydrogen, lower alkoxy or an optionally substituted methyl group and wherein, if the radicals $R_1$ and $R_2$ are separate, $R_1$ is hydrogen and $R_2$ is optionally substituted phenyl, thienyl or furyl and, if the radicals $R_1$ and $R_2$ are linked, they form, together with the carbon atom, an optionally substituted cycloalkyl ring with 4 to 7 carbon atoms, and wherein n and m independently of one another represent 0 or 1 and B represents an optionally substituted 2,6-dioxo- or 2,6-dithioxo-1,2,3,6-tetrahydropyrimidyl, 2-thioxo-6-oxo-1,2,3,6-tetrahydropyrimidyl, 2,6-dihydroxy- or 2,6-dimercapto-pyrimidyl, 2-mercapto-6-hydroxypyrimidyl, 2,6-diaminopyrimidyl, 2-amino-6-hydroxy-pyrimidyl or 2,6-dihalogenopyrimidyl radical, these radicals being bonded in the 4- or 5-position.

Preferably, n represents 1 and m represents 0. Substituents of the abovementioned cyclic radicals $R_2$ or $R_1+R_2$ are, for example, lower alkyl, such as methyl, lower alkoxy, such as methoxy, halogen atoms, for example fluorine or chlorine, trifluoromethyl, the nitro group and above all carbamoyl and acyl, especially lower alkanoyl, such as acetyl. The cyclic radicals are preferably unsubstituted. $R_1+R_2$ represent, together with the carbon atom, above all cyclopentyl, cyclohexyl or cyclohexenyl. If $R_2$ represents thienyl or furyl, these radicals are bonded in the 2- or 3-position, preferably in the 2-position.

Above all, $R_1$ represents hydrogen and $R_2$ represents unsubstituted phenyl.

The following general formulae

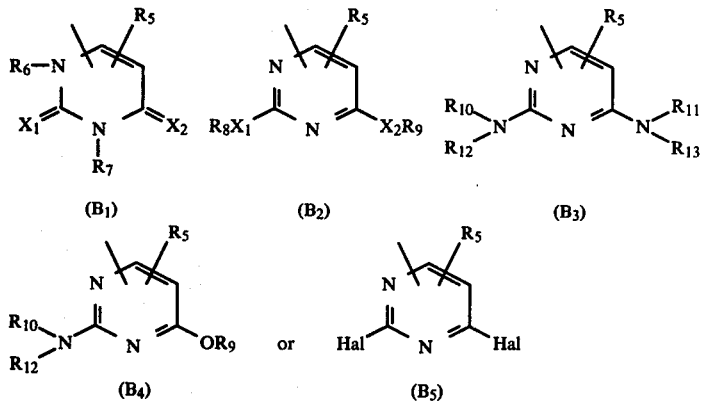

can be written for the radical B; in these, $X_1$ represents oxygen or sulphur and $X_2$ represents oxygen or, if $X_1$ represents sulphur, $X_2$ can also denote sulphur. Preferably, $X_1$ and $X_2$ represent oxygen. The substituent $R_5$ can be in the 5- or 4-position depending on whether the radical B is bonded in the 4- or 5-position.

$R_5$ represents hydrogen, halogen, especially chlorine or fluorine, or an optionally substituted aliphatic or aromatic hydrocarbon radical.

An optionally substituted aliphatic hydrocarbon radical $R_5$ is above all a lower alkyl radical, especially a radical with 1-4 carbon atoms such as methyl, ethyl, propyl, isopropyl, n-butyl or tert.butyl. The radical can be substituted by one or more substituents. As substituents there should in particular be mentioned free, esterified or etherified hydroxyl or mercapto groups, such as halogen, acyloxy, above all lower alkanoyloxy, such as acetoxy, or aroyloxy, such as benzoyloxy, lower alkoxy, such as methoxy, aryloxy, such as phenoxy which is optionally substituted, in particular by halogen, nitro, lower alkyl or lower alkoxy, for example p-chlorophenoxy, or lower alkylmercapto, such as methylmercapto.

An optionally substituted aromatic hydrocarbon radical $R_5$ is a monocyclic or bicyclic radical, for example naphthyl or preferably phenyl. These radicals can be substituted in the same manner as the aliphatic radicals or can be substituted by lower alkyl. Examples which should be mentioned are p-nitrophenyl or m-methoxyphenyl.

$R_5$ above all represents hydrogen.

$R_6$ and $R_7$ independently of one another represent hydrogen, or an optionally substituted aliphatic hydrocarbon radical. These hydrocarbon radicals and their substituents are the same as indicated above for the corresponding radicals $R_5$. Preferably, $R_6$ and $R_7$ denote hydrogen and/or lower alkyl with 1–4 carbon atoms such as ethyl, propyl, isopropyl or tert.butyl, but especially methyl. Above all, $R_6$ and $R_7$ both represent hydrogen.

$R_8$ and $R_9$ also independently of one another represent hydrogen or an optionally substituted aliphatic hydrocarbon radical, with the hydrocarbon radicals and the substituents having the same meaning as indicated above for corresponding $R_5$ radicals. Preferably, $R_8$ and $R_9$ both represent hydrogen.

$R_{10}$, $R_{11}$, $R_{12}$ and $R_{13}$ independently of one another represent hydrogen or an organic radical having the meaning of $R_8$ and $R_9$.

In the formula $B_5$, "Hal" represents a halogen atom, especially fluorine and above all chlorine.

The substituent $R_3$ present in the penicillanic acid and cephalosporanic acid derivatives of the formula Ia and Ib is, as mentioned, a free or therapeutically usable esterified carboxyl group, for example an ester group which can be split enzymatically.

Esters which can be split enzymatically are above all those which contain an ester group which can be split under physiological conditions. These esters can readily be resorbed in the organism and are therefore therapeutically usable as such. Esters of this nature are described, for example, in British Pat. No. 1,229,453, in Belgian Pat. No. 789,821 and in German Offenlegungsschrift DT No. 1,951,012, DT No. 2,228,012 and DT No. 2,230,620. Such esters are derived, for example, from 5-hydroxyindanol or 3,4-benzo-5-oxo-tetrahydro-2-furanol or from alcohols of the formula HO—CH$_2$OCO—$R_3''$, wherein $R_3''$ can represent an alkyl radical or an aminoalkyl radical or a cycloalkyl radical with 3—7 carbon atoms. In particular, $R_3''$ denotes a lower alkyl radical, such as methyl, ethyl, or isopropyl but above all tert.butyl, an α-amino-lower alkyl radical, such as 1-amino-2-methylpropyl or 1-amino-3-methylbutyl, a cyclopentyl radical or cyclohexyl radical.

The radical $R_4$ in the cephalosporanic acid derivatives of the formula Ib represents, as mentioned, a hydrogen atom, (in which case the side chain in the 3-position of cephalosporin C is absent), lower alkoxy, especially methoxy (compare U.S. Pat. application, Ser. No. 373,818) or an unsubstituted or substituted methyl group. Substituents of the methyl group are, above all, a free, esterified or etherified hydroxyl or mercapto group, an optionally N-substituted carbamoyloxy or thiocarbamoylmercapto group, or above all a quaternary ammonium group, and also the nitrile group, An esterified hydroxyl or mercapto group contains, as the acid radical, above all the radical of a carboxylic acid or thiocarboxylic acid, for example lower alkanoyl which is optionally substituted by halogen atoms, especially chlorine, such as formyl, propionyl, butryl, pivaloyl, chloroacetyl, but especially acetyl, or aroyl or aryl-lower alkanoyl which are optionally substituted, for example by lower alkyl, lower alkoxy, halogen or nitro, for example benzoyl or phenylacetyl, and also, as a thiocarboxylic acid radical, in particular aroylthio which is optionally substituted as mentioned, above all benzoylthio. Additionally, hydroxyl groups esterified by hydrogen halide acids should be mentioned; the methyl group $R_4$ can therefore be substituted by, for example, fluorine, chlorine or bromine.

Examples of etherified hydroxyl groups are described in Belgian Pat. No. 719,710. Lower alkoxy, such as methoxy, ethoxy or n-propoxy, should be singled out.

Etherified mercapto groups contain, as etherifying radicals, for example, lower alkyl, for example methyl, and also optionally substituted phenyl or heterocyclyl. Phenyl can be substituted, by, for example, lower alkyl, lower alkoxy, halogen or nitro. The heterocyclyl radicals preferably possess 5–6 ring atoms and contain, as hetero-atoms, nitrogen which is optionally in the N-oxidised form, and/or oxygen or sulphur. Examples to be mentioned are 1-oxidised 2-pyrimidyl, pyridazinyl, pyrazinyl, imidazolyl, imidazolidyl and purinyl. These radicals can be substituted, for example by lower alkyl, lower alkoxy, hydroxyl or halogen. Optionally substituted heterocyclyl radicals of aromatic character with 5 ring atoms, which contain 2 nitrogen atoms and at least one further hetero-atom from the group of nitrogen, oxygen and sulphur, should be singled out particularly. Preferred substituents are lower alkyl radicals with 1–5 carbon atoms, such as methyl, ethyl, propyl, isopropyl, n-butyl, isobutyl or tert.butyl, lower alkoxy or lower alkylthio radicals with 1–5 carbon atoms, especially methylthio, cycloalkyl radicals such as cyclopentyl or cyclohexyl, or aryl radicals such as phenyl or substituted phenyl, for example phenyl substituted by one or more nitro groups or halogen atoms or lower alkyl or lower alkoxy groups, or unsubstituted or substituted thienyl, especially thienyl-(2) or thienyl substituted as indicated for phenyl, or optionally monosubstituted or disubstituted amino groups, for example acetylamino, tert.butoxycarbonylamino, tert.amyloxycarbonylamino or sulphonylamino.

As examples of the heterocyclyl radical there should be mentioned: 1H-1,2,3,Triazol-5-yl, 1,3,4-triazol-2-yl, 5-methyl-1,3,4-triazol-2-yl, 1H-1,2,4-triazol-5-yl, 1-phenyl-3-methyl-1H-1,2,4-triazol-5-yl, 4,5-dimethyl-4H-1,2,4-triazol-3-yl, 4-phenyl-4H-1,2,4-triazol-3-yl, 1H-tetrazol-5-yl, 1-methyl-1H-tetrazol-5-yl, 1-ethyl-1H-tetrzol-5-yl, 1-n-propyl-1H-tetrazol-5-yl, 1-isopropyl-1H-tetrazol-5-yl, 1-n-butyl-1H-tetrazol-5-yl, 1-cyclopentyl-1H-tetrazol-5-yl, 1-phenyl-1H-tetrazol-5-yl, 1-p-chlorophenyl-1H-tetrazol-5-yl, 1,2,3-thiadiazol-5-yl, 1,3,4-thiadiazol-2-yl, 1,2,4-thiadiazol-3-yl, 1,2,4-thiadiazol-5-yl, 3-methyl-1,2,4-thiadiazol-5-yl, 2-methyl-1,3,4-thiadiazol-5-yl, 2-methylthio-1,3,4-thiadiazol-5-yl, 2-ethyl-1,3,4-thiadiazol-5-yl, 2-n-propyl-1,3,4-thiadiazol-5-yl, 2-isopropyl-1,3,4-thiadiazol-5-yl, 2-phenyl-1,3,4-thiadiazol-5-yl, 1,2,4-oxadiazol-5-yl, 1,2,3-oxadiazol-5-yl, 1,3,4-oxadiazol-5-yl, 2-methyl-1,3,4-oxadiazol-5-yl, 2-ethyl-1,3,4-oxadiazol-5-yl, 2-phenyl-1,3,4-oxadiazol-5-yl, 2-p-nitrophenyl-1,3,4-oxadiazol-5-yl, 2-[thienyl(2)]-1,3,4-oxadiazol-5-yl and thiatriazol-5-yl.

An optionally N-substituted carbamoyloxy group or thiocarbamoylmercapto group is, for example, a group of the formula —O—CO—NH—$R_{17}$ (French Pat. No. 1,463,831) or

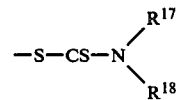

wherein R₁₇ is an optionally halogen-substituted lower alkyl radical and R₁₈ is hydrogen or R₁₇ (compare J. Med. Chem. 8, 174 (1965). Above all, R₁₇ is methyl, ethyl or chlorine-substituted methyl or ethyl, especially β-chloroethyl.

In a quaternary ammonium-methyl group R₄, the ammonium part is preferably an unsubstituted or substituted pyridinium group, especially an unsubstituted pyridinium group.

Examples of substituents of the pyridinium group which should be mentioned are those listed in Antimicrobial Agents and Chemotherapy 1966, pages 573–580, such as unsubstituted or substituted, for example hydroxy-substituted or carboxy-substituted, lower alkyl, for example methyl, ethyl, propyl, hydroxymethyl or carboxymethyl, halogen, such as fluorine, chlorine, bromine or iodine, or trifluoromethyl, hydroxyl, sulpho, carboxyl, nitrile, lower alkoxycarbonyl, such as methoxycarbonyl or ethoxycarbonyl, lower alkylcarbonyl, such as methylcarbonyl, and especially unsubstituted or substituted carbamoyl, for example carbamoyl substituted by lower alkyl, hydroxy-lower alkyl or halogeno-lower alkyl, especially chloro-lower alkyl, such ad N-methylcarbamoyl, N-isopropylcarbamoyl, N-β-chloroethylcarbamoyl and above all carbamoyl. The substituents can be in the 2-, 3- and/or 4-position, and are preferably in the 3- or 4-position.

Salts of compounds of the present invention are above all pharmaceutically usable, non-toxic salts of compounds which are capable of forming salts with bases. Such salts are above all metal salts or ammonium salts, such as alkali metal salts, alkaline earth metal salts and earth metal salts, for example sodium, potassium, magnesium, calcium or aluminium salts, and also ammonium salts with ammonia or suitable organic amines; above all, it is possible to use for salt formation aliphatic, cycloaliphatic, cycloaliphatic-aliphatic and araliphatic primary, secondary or tertiary monoamines, diamines or polyamines as well as heterocyclic bases, such as lower alkylamines, for example triethylamine, hydroxy-lower alkylamines, for example 2-hydroxyethylamine, bis-(2-hydroxyethyl)-amine or tri-(2-hydroxyethyl)-amine, basic aminoacids such as lysine, ornithine or arginine, basic aliphatic esters of carboxylic acids, for example 4-aminobenzoic acid 2-diethylaminoethyl ester, lower alkyleneamines, for example 1-ethylpiperidine, cycloalkylamines, for example bicyclohexylamine, or benzylamines, for example N,N'-dibenzyl-ethylenediamine and also bases of the pyridine type, for example pyridine, collidine or quinoline.

The new compounds can be in the form of mixtures of isomers, for example racemates, or of individual isomers, for example optically active antipodes.

The new compounds of the formula I display a pharmacological action, especially a particularly pronounced antibacterial action. Thus they are active against Gram-positive bacteria, such as Staphylococcus aureus, but above all against Gram-negative bacteria, for example Escheria coli, Klebsiella pneumonia and Salmonella typhosa, and especially against Bacterium proteus and Pseudomonas aeruginosa. Thus they inhibit the growth of Pseudomonas aeruginosa at dilutions down to 0.4 γ/ml. They can therefore be used for combating infections which are caused by such microorganisms and can also be used as fodder additives, for the preservation of foodstuffs or as disinfectants.

Compounds to be singled out are 3-cephem compounds of the formula

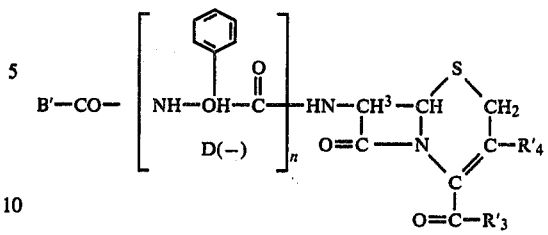

and especially pneum compounds of the formula

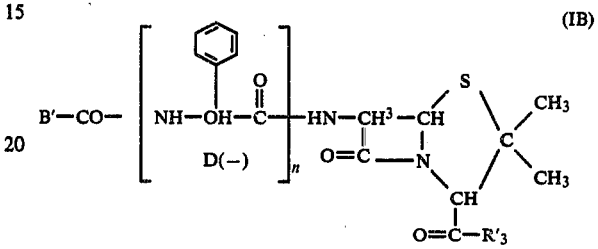

(IB)

wherein R₃' represents hydroxyl and R₄' represents hydrogen, methyl, methoxy, lower alkanoyloxymethyl, for example acetoxymethyl, or pyridiniummethyl, 1-oxidised 2-pyridylthiomethyl, 1,3,4-thiadiazol-2-ylthiomethyl, 2-methyl-1,3,4-thiadiazol-5-ylthiomethyl, 3-methyl-1,2,4-thiadiazol-5-ylthiomethyl or 1-methyl-5-tetrazolylthiomethyl which are optionally substituted by lower alkyl, hydroxyl, halogen, carboxyl or above all carbamoyl, and wherein n represents 0 or 1 and B' represents a radical of the formula B₁ bonded in the 4- or 5-position, in which radical R₆ and R₇ enote hydrogen and R₅ denotes lower alkyl, halogen, phenyl or above all hydrogen.

Compounds which are therapeutically particularly valuable are penam compounds of the formula IB, wherein B' has the indicated meaning and R₃' represents hydroxyl, such as 6-[D(−)-α-(1,2,3,6-tetrahydro-2,6-dioxo-4-pyrimidinecarboxamido)phenylacetamido]-penicillanic acid and 6[D(−)-α-(1,2,3,4-tetrahydro-2,4-dioxo-5-pyrimidinecarboxamido)-phenylacetamido]-penicillanic acid and corresponding cephalosporanic acid compounds and non-toxic salts, such as alkali metal salts, for example sodium salts, or alkaline earth metal salts, such as calcium salts, of these compounds, and also cephem compounds of the formula IA, wherein B' has the indicated meaning, R₃ represents hydroxyl and R₄' represents pyridiniummethyl, such as 7-[D(−)-α-(1,2,3,6-tetrahydro-2,6-dioxo-4-pyrimidinecarboxamido)-phenylacetamido]-ceph-3-em-pyridiniummethyl-4-carboxylic acid, 7-[D(−)-α-(1,2,3,4-tetrahydro-2,4-dioxo-5-pyrimidinecarboxamido)-phenylacetamido]-ceph-3-em-3-pyridiniummethyl-4-carboxylic acid and 7-[D(−)-α-(1,2,3,4-tetrahydro-2,4-dioxo-5-pyrimidinecarboxamido)-phenylacetamido]-ceph-3-em-3-[1-carbamoyl-pyridiniomethyl)]-ceph-3-em-4-carboxylic acid and their salts.

The new compounds are manufactured according to methods which are in themselves known. Thus they are obtained when a compound of the formula II

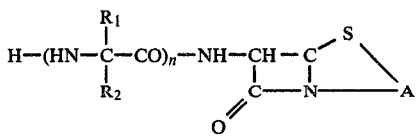

wherein $R_1$, $R_2$, A and n have the indicated meaning and wherein a free carboxyl group $R_3$ which may be present in the radical A is optionally protected, or a salt thereof, is acylated with the acid of the formula III

wherein B and m have the indicated meaning, or with a reactive derivative of this acid. The compounds of the formula II, wherein n represents 1, can also be obtained by acylation of the compound II'

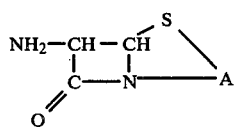

wherein A has the indicated meaning and wherein a free carboxyl group $R_3$ which may be present in the radical A is optionally protected, or of a salt thereof, with the acid of the formula III'

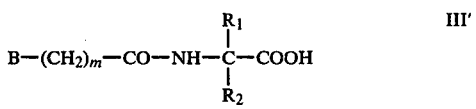

wherein $R_1$, $R_2$, B and m have the indicated meaning, or with a reactive derivative of this acid. If a protective group is present in a compound of the formula Ia or Ib obtained according to one of the two processes, it can be split off in a known manner. If desired, a free carboxyl group $R_3$ present in a product of the formula Ia or Ib can be converted into a therapeutically usable ester group $R_3$ and/or, if desired, an optionally substituted methyl group $R_4$ can be converted into another group $R_4$ and/or, if desired, a compound obtained as the free acid can be converted into a salt or a salt obtained can be converted into the free acid and/or an isomer mixture obtained can be separated into the individual isomers.

A free carboxyl group $R_3$ in a starting material of the formula II or II' can in particular be protected by esterification. The ester groups used are in particular those which can be split to the free carboxyl group in an acid or weakly alkaline medium, solvolytically, for example by hydrolysis or alcoholysis, hydrolytically, reductively or by nucleophilic exchange.

Ester groups which can easily be split by solvolysis with a solvent containing hydroxyl groups, for example water or alcohols such as, for example, methanol or ethanol, preferably under neutral conditions, are above all those which are derived from silyl alcohol or stannyl alcohol. Such groups are described, for example, in British Patent Nos. 1,073,530 and 1,211,694, and in German Offenlegungsschrift No. 1,800,698.

Esters which are easily split in an acid medium, for example in the presence of hydrogen chloride, hydrogen fluoride or hydrogen bromide or in the presence of organic acids such as acetic acid, trifluoroacetic acid, formic acid or their mixtures with water are above all esters which are derived from lower alkanols which are poly-branched in the α-position or from lower alkanols which contain one or more electron donors in the α-position. Examples of such ester groups are tert.butoxycarbonyl, tert.amyloxycarbonyl, cyclopentyloxycarbonyl, cyclohexyloxycarbonyl, adamantyloxycarbonyl, furfuryloxycarbonyl, p-nitrobenzyloxycarbonyl, p-methoxybenzyloxycarbonyl, diphenylmethoxycarbonyl and pivaloyloxymethoxycarbonyl. Ester groups which can be split by reduction, for example with zinc and acetic acid, are above all derived from 2-halogenolower alkanols, for example from 2,2,2-trichloroethanol, 2-chloroethanol, 2-bromoethanol and 2-iodoethanol.

Salts of starting substances of the formula II are especially those of compounds possessing a free carboxyl group, above all ammonium salts, such as tri-lower alkylammonium salts, for example triethylammonium salts, and also alkali metal salts.

The acylation of the compound II or II' with the acyl radical III or III' is carried out according to methods which are in themselves known, especially in the manner known from peptide chemistry for the acylation of weakly basic amino groups. The acylating agent used which contains the acyl radical III or III' is either the corresponding acid, in which case the reaction is carried out in the presence of a condensation agent, for example of a carbodiimide such as dicyclohexylcarbodiimide, or of Woodward Reagent K or L, or is a reactive acid derivative, above all an acid halide, especially an acid chloride or bromide, and also, for example, an acid azide, an activated ester or a mixed anhydride, for example an anhydride with mono-esterified carbonic acid, such as a carbonic acid lower alkyl ester, for example carbonic acid methyl ester, or with an optionally halogen-substituted lower alkanoic acid such as formic acid or pivalic acid or trichloroacetic acid. Examples of activated esters are p-nitrophenyl esters, 2,4-dinitrophenyl esters, 2,4,5- or 2,4,6-trichlorophenyl esters, pentachlorophenyl esters and also, for example, the cyanomethyl ester, N-hydroxysuccinimide ester, N-hydroxypiperidine ester and N-hydroxyphthalimide ester.

The acylation reaction is carried out in the presence of a solvent or diluent, if desired in the presence of a catalyst and/or in the presence of basic agents such as aliphatic, aromatic or heterocyclic nitrogen bases, for example triethylamine, diisopropylethylamine, N,N-diethylaminoacetic acid ethyl ester, N-ethyl-morpholine, N,N-dimethylaniline, pyridine, 2-hydroxypyridine, p-dimethylaminopyridine, collidine or 2,6-lutidine.

The reaction is carried out at room temperature or with cooling or warming, for example at temperatures of −70° to +100° C., optionally in an inert gas atmosphere, for example a nitrogen atmosphere, and/or with exclusion of moisture.

The acylating agents are known or can be manufactured in a manner which is in itself known.

During the acylation reaction, it is desirable to protect free hydroxyl, mercapto, amino and/or carboxyl groups which may be present in the reactants, especially by easily removable protective groups, such as are known, for example, from peptide synthesis, compare Schröder and Lübke "The Peptides", Vol. I. Academic Press, New York and London, 1965, and Th. Wieland, Angew. Chem. 63 (1951) 7–14, 66 (1954), 507–512, 69 (1957), 362–372, 71 (1959), 417–425 and 75 (1963), 539–551. As examples of amino protective groups there should be mentioned optionally substituted aralkyl groups, such as diphenylmethyl or triphenylmethyl groups, or acyl groups such as formyl, trifluoroacetyl, phthaloyl, p-toluenesulphonyl, benzylsulphonyl, benzenesulphenyl, o-nitrophenylsulphenyl or above all groups derived from carbonic acid or thiocarbonic acid, such as carbobenzoxy groups optionally substituted in the aromatic radical by halogen atoms, nitro groups, lower alky or lower alkoxy or lower carbalkoxy groups, for example carbobenzoxy, p-bromocarbobenzoxy or p-chlorocarbobenzoxy, p-nitrocarbobenzoxy, p-methoxycarbobenzoxy, coloured benzyloxycarbonyl groups, such as p-phenylazo-benzyloxycarbonyl and p-(p'-methoxyphenylazo)-benzyloxycarbonyl, tolyloxycarbonyl, 2-phenyl-isopropoxycarbonyl, 2-tolyl-isopropoxycarbonyl and above all 2-(para-biphenylyl)-2-propoxycarbonyl, and also aliphatic oxycarbonyl groups such as, for example, allyloxycarbonyl, cyclopentyloxycarbonyl, tert.amyloxycarbonyl, adamantyloxycarbonyl, 2,2,2-trichloroethoxycarbonyl, 2-iodo-ethoxycarbonyl and above all tert.butoxycarbonyl, as well as, for example, carbamoyl, thiocarbamoyl, N-phenylcarbamoyl and N-phenylthiocarbamoyl. Easily removable ester groups for protecting a free carboxyl group have already been listed above. Hydroxyl groups are preferably protected by etherification, for example with tert.butanol. As example of a suitable mercapto protective group is trityl.

In a compound of the formula I obtained according to the invention, a protected carboxyl group $R_3$, especially an esterified carboxyl group which can easily be converted into the free carboxyl group, can be converted in the abovementioned manner into the free carboxyl group. It is also possible, before splitting off the ester group, to convert the ester group into a different ester group, for example to convert a 2-bromoethyl ester group into a 2-iodoethyl ester group.

In compounds of the formula I, wherein the fragment —S—A— represents the group of the formula Ib, a radical $R_4$ can be converted into another group of this type. Thus it is possible to treat a compound with an esterified hydroxymethyl radical $R_4$, wherein the esterified hydroxyl group in particular denotes lower alkanoyloxy, for example acetoxy, with pyridine at elevated temperature, or first to react it with thiobenzoic acid and then to treat it with pyridine in the presence of a mercury salt, or to react it with a suitable salt, such as potassium thiocyanate, potassium iodide or potassium nitrate, and with pyridine in the presence of water at a pH value of about 6.5 which is obtained, for example, by means of phosphoric acid, and thus to obtain the corresponding pyridiniummethyl compound which can, if necessary, be coverted into the inner salt (zwitter-ion form), for example by treatment with a suitable ion exchange reagent. The pyridinium compound can also be manufactured according to the process of Belgian Pat. No. 719,711 (DOS No. 1,795,643) by first converting the acetoxy group into a group more suitable for nucleophilic replacement, for example a halogen atom or an acetoxy group possessing an electron-attracting substituent, such as, for example, chloroacetoxy, dichloroacetoxy or cyanoacetoxy. Furthermore it is possible to react compounds having a lower alkanoyloxymethyl group, for example an acetoxymethyl group, as the radical $R_4$, with a mercapto compound, such as an optionally substituted lower alkylmercaptan, phenylmercaptan or heterocyclylmercaptan and thus to obtain compounds of the formula I, wherein $R_4$ is a partial formula Ib represents an etherified mercapto group.

Salts of compounds of the formula I can be manufactured in a manner which is in itself known. Thus it is possible to form salts of compounds of the formula I, wherein $R_3$ represents a free carboxyl group by, for example, treatment with metal compounds such as alkali metal salts of suitable carboxylic acids, for example the sodium salt of α-ethyl-caproic acid, or with ammonia or a suitable organic amine.

Salts can be converted in the usual manner into the free compounds, in the case of metal salts and ammonium salts by, for example, treatment with suitable acids or ion exchange exchangers.

Mixtures of isomers which are obtained can be separated into the individual isomers according to methods which are in themselves known, for example by fractional crystallisation, adsorption chromatography (column chromatography or thin layer chromatography) or other suitable methods of separation. Resulting racemates can be separated into the antipodes in the usual manner, if appropriate after introducing of suitable salt-forming groups, for example by forming a mixture of diastereoisomeric salts with optically active salt-forming agents, separating the mixture into the diastereoisomeric salts and converting the separated salts into the free compounds, or by fractional crystallisation from optically active solvents.

The process also encompasses embodiments according to which compounds which arise as intermediate products are used as starting substances and the remaining process steps are carried out with these, or the process is stopped at any stage; furthermore, starting substances can be used in the form of derivatives or be formed during the reaction.

Preferably, such starting substances are used, and the reaction conditions are so chosen, as to give the compounds initially mentioned as being particularly preferred.

The starting substances of the formula II are known or can be manufactured according to the processes already mentioned.

The new compounds can be used as medicines, for example in the form of pharmaceutical preparations which contain an effective amount of the active substance together with, or mixed with, inorganic or organic, solid or liquid, pharmaceutically usable excipients which are suitable for enteral or, preferably, parenteral administration. Thus, tablets or gelatine capsules are used which contain the active compound together with diluents, for example lactose, dextrose,, sucrose, mannitol, sorbitol, cellulose and/or glycine, and lubricants, for example, silica, talc, stearic acid or salts thereof, such as magnesium stearate or calcium sterate, and/or polyethylene glycol; tablets also contain binders, for example magnesium aluminium silicate, starches, such as corn starch, wheat starch, rice starch or arrowroot, gelatine, tragacanth, methylcellulose, sodium carboxymethylcellulose and/or polyvinylpyrrolidone and, if desired, disintegrating agents, for example starches, agar, alginic acid or a salt thereof, such as sodium alginate, and/or effervescing mixtures, or adsorbents, dyestuffs, flavouring substances and sweeteners. Preferably, the pharmacologically active compounds of the present invention are used in the form of injectable preparations, for example of preparations which can be administered intravenously, or of infusion solutions. Such solutions are preferably isotonic aqueous solutions or suspensions, and these can be manufactured before use, for example from lyophilised preparations which contain the active substance by itself or together with an excipient, for example mannitol. The pharmacological preparations can be sterilised and/or contain auxiliaries, for example preservatives, stabilisers, wetting agents and/or emulsifiers, solublising agents, salts for regulating the osmotic pressure and/or buffers. The present pharmaceutical preparations which can, if desired, contain further pharmacologically valuable substances, are prepared in a manner which is in itself known, for example by means of conventional mixing, granulating, dragee-making, dissolving or lyophilising processes, and contain from about 0.1% to 100%, and especially from about 1% to about 50%, of lyophilisates and up to 100% of the active substance.

In the context of the present description, organic radicals described as "lower" contain up to 6, preferably up to 4, carbon atoms; acyl radicals contain up to 20, preferably up to 12, carbon atoms.

The examples which follow serve to illustrate the invention.

The following systems are used in thin layer chromatography:
System 52A n-butanol/glacial acetic acid/water (67:10:23)
System 67 n-butanol/ethanol/water (40:10:50, upper phase)
System 101 n-butanol/pyridine/glacial acetic acid/water (38:24:30)
System 101A n-butanol/pyridine/glacial acetic acid/water (42:24:4:30)

In the Examples the $ED_{50}$ means the concentration in mg/kg (mouse, subcutaneous, once on infection and once 3 hours later) at which 50% of the animals infected with a lethal doses of Pseudomonas aeruginose ATCC 12055 survive.

EXAMPLE 1:

A suspension of 4.38 g of anhydrous 6-[D(−)-phenylglycylamino]-penicillanic acid in 120 ml of methylene chloride is treated with 2.60 ml of triethylamine whilst stirring and excluding moisture and is then cooled to 0° C. A solution of 4.33 g of orotic acid chloride (manufactured according to the method of D. G. Crosby and R. V. Berthold, 7, Med. Chem. 6, 334 (1963) and freed from unreacted orotic acid by dissolving in tetrahydrofurane) in 240 ml of absolute tetrahydrofurane is then added dropwise to the clear solution at 0° C. over the course of 20 minutes, whilst stirring and cooling in an ice bath. The reaction mixture is stirred for 30 minutes at 0° C. and 45 minutes at room temperature. 300 ml of phosphate buffer solution of pH 7.5 are then added, the solvent is evaporated off on a rotary evaporator at 45° C. and the phosphate buffer solution is twice extracted with ethyl acetate. The clear aqueous phase is covered with ethyl acetate, acidified (pH 2.5) at 10° C. by adding 20% strength phosphoric acid whilst stirring and cooling with an ice bath, and exhaustively extracted with ethyl acetate. The ethyl acetate extracts are combined, washed with sodium chloride solution and dried over sodium sulphate, and the solvent is evaporated off on a rotary evaporator at 45° C. The product which remains (3.70 g; 61% of theory) is crystallized from a mixture of tetrahydrofurane and ether. 6-[D(−)-α-(1,2,3,6-Tetrahydro-2,6-dioxo-4-pyrimidinecarboxamido)-phenylacetamido]-penicillanic acid melts, with decomposition, at 213°–215° C.

Thin layer chromatogram on silica gel: $Rf_{52A}=0.60$, $Rf_{101}=0.52$, $Rf_{67}=0.30$, $Rf_{101A}=0.50$. $[\alpha]_D^{20}=+166°\pm1°$ (c=0.924 in dimethylsulphoxide). $ED_{50}=35$.

EXAMPLE 2:

7-[D(−)-α-(1,2,3,6-Tetrahydro-2,6-dioxo-4-pyridimidinecarboxamido)-phenylacetamido]-cephalosporanic acid is obtained by reaction of 4.05 g of D(−)-cephaloglycine in 70 ml of methylene chloride with a solution of 3.49 g of orotic acid chloride in 100 ml of absolute tetrahydrofurane in the presence of 2.10 ml of triethylamine, as in Example 1. The crude product (3.14 g; 58% of theory) is purified by crystallisation from a mixture of tetrahydrofurane and ether. Melting point 263°–266° C., with decomposition.

Thin layer chromatogram on silica gel: $Rf_{52A}=0.31$, $Rf_{101}=0.57$, $Rf_{67}=0.28$, $Rf_{101}=0.52$. $ED_{50}=100$.

EXAMPLE 3:

6-[D(−)-α-(2,6-Dichloro-4-pyrimidinecarboxamido)-phenylacetamido]-penicillanic acid is obtained according to the process of Example 1 by reaction of 6-[D(−)-phenylglycylamino]-penicillanic acid with 2,6-dichloro-4-pyrimidinecarboxylic acid chloride in methylene dichloride in the presence of triethylamine. The product, dissolved in ethyl acetate, is filtered through silica gel and is precipitated with a mixture of ether and petroleum ether. Melting point 151°–155° C. (decomposition). $[\alpha]_D^{20}=+136°\pm1°$ (c=1.056 in dimethylsulphoxide). Thin layer chromatogram on silica gel: $Rf_{52A}=0.77$; $Rf_{67}=0.42$; $Rf_{101}=0.36$; $Rf_{101A}=0.31$.

EXAMPLE 4:

6-[D(−)-α-(5-n-Butyl-1,2,3,6-tetrahydro-2,6-dioxo-4-pyrimidinecarboxamido)-phenylacetamido]-penicillanic acid is obtained according to the process of Example 1 by reaction of 6-[D(−)-phenylglycylamino]-penicillanic acid with 5-butylorotic acid chloride in methylene chloride in the presence of triethylamine. The product is precipitated from ethyl acetate solution by means of a mixture of ether and petroleum ether. Melting point 177°–180° C. (decomposition). $[\alpha]_D^{20}=+150°\pm1°$ (c=0.875 in dimethylsulphoxide). Thin layer chromatogram on silica gel: $Rf_{52A}=0.67$; $Rf_{67}=0.42$; $Rf_{101}=0.58$; $Rf_{101A}=9.57$.

EXAMPLE 5:

6-[D(−)-α-(5-Phenyl-1,2,3,6-tetrahydro-2,6-dioxo-4-pyrimidinecarboxamido)-phenylacetamido]-penicillanic acid is obtained according to the process of Example 1 by reaction of 6-[D(−)-phenylglycylamino]-penicillanic acid with 5-phenylorotic acid chloride in methylene chloride in the presence of triethylamine. The product is precipitated from methanol solution by means of ether. Melting point 199°–202° C. (decomposition). $[\alpha]_D^{20}=+111°\pm1°$ (c=1.027 in dimethylsulphoxide). Thin layer chromatogram on silica gel: $Rf_{52A}=0.61$; $Rf_{67}=0.35$; $Rf_{101}=0.59$; $Rf_{101A}=0.57$.

EXAMPLE 6

6-[D(−)-α-(2,6-Dimethoxy-4-pyrimidinecarboxamido)-phenylacetamido]-penicillanic acid is obtained according to the process of Example 1 by reaction of 6-[D(−)-phenylglycylamino]-penicillanic acid with 2,6-dimethoxy-4-pyrimidinecarboxylic acid chloride in methylene chloride in the presence of triethylamine. The product, dissolved in ethyl acetate, is filtered through silica gel and is precipitated with a mixture of ether and petroleum ether. Melting point 150°–153° C. (decomposition). $[\alpha]_D^{20} = +176° \pm 1°$ (c=0.847 in dimethylsulphoxide). Thin layer chromatogram on silica gel: $Rf_{52A}=0.68$; $Rf_{67}=0.38$; $Rf_{101}=0.57$; $Rf_{101A}=0.52$.

EXAMPLE 7

6-[D(−)-α-(1-Methyl-1,2,3,6-tetrahydro-2,6-dioxo-4-pyrimidinecarboxamido)-phenylacetamido]-penicillanic acid is obtained according to the process of Example 1 by reaction of 6-[D-(−)-phenylglycylamino]-penicillanic acid with 1-methylorotic acid chloride in a mixture of methylene chloride, tetrahydrofurane and dioxane in the presence of triethylamine. The product is precipitated from ethyl acetate solution by means of petroleum ether. Melting point 182°–186° C. (decomposition). $[\alpha]_D^{20} = +167° \pm 1°$ (c=0.908 in dimethylsulphoxide). This layer chromatogram on silica gel: $Rf_{52A}=0.58$; $Rf_{67}=0.33$; $Rf_{101}=0.56$; $Rf_{101A}=0.53$.

EXAMPLE 8

6-[D(−)-α-(1,2,3,4-Tetrahydro-2,4-dioxo-5-pyrimidinecarboxamido)-phenylacetamido]-penicillanic acid is obtained according to the process of Example 1 by reaction of 6-[D(−)-phenylglycylamino]-penicillanic acid with uracil-5-carboxylic acid chloride. The product is precipitated from ethyl acetate solution by means of petroleum ether. Melting point 205°–210° C. (decomposition). $[\alpha]_D^{20} = +174° \pm 1°$ (c=0.648 in dimethylsulphoxide). Thin layer chromatogram on silica gel: $Rf_{52A}=0.56$; $Rf_{67}=0.33$; $Rf_{101}=0.55$; $Rf_{101A}=0.51$. $ED_{50}=70$.

EXAMPLE 9

7-[D(−)-α-(1,2,3,4-Tetrahydro-2,4-dioxo-5-pyrimidinecarboxamido)-phenylacetamido]-cephalosporanic acid is obtained according to the process of Example 1 by reaction of 7-[D(−)phenylglycylamino]-cephalosporanic acid with uracil-5-carboxylic acid chloride. The product is purified by recrystallisation from methanol, Melting point 300°–305° C. (decomposition). In a thin layer chromatogram on silica gel $Rf_{52A}=0.31$; $Rf_{67}=0.26$; $Rf_{101}=0.53$; $Rf_{101A}=0.50$. $[\alpha]_D^{20}=+35° \pm 1°$ (c=0.985 in dimethylsulphoxide). UV-spectrum: $\lambda_{max}=275$ nm (c=20,000); $\lambda_{min}=243$ nm ($\epsilon=11,400$ (in methanol). $ED_{50}=30$.

EXAMPLE 10

6-[D(−)-α-(5-Chloro-1,2,3,6-tetrahydro-2,6-dioxo-4-pyrimidinecarboxamido)-phenylacetamido]-penicillanic acid is obtained according to the process of Example 1 by reaction of 6-[D(−)-phenylglycylamino]-pencillanic acid with 5-chloroorotic acid chloride. $[\alpha]_D^{20}=+153° \pm 1°$ (c=0.747 in dimethylsulphoxide. $Rf_{52A}=0.66$; $Rf_{67}=0.26$; $Rf_{101}=0.55$; $Rf_{101A}=0.60$.

EXAMPLE 11

7-(1,2,3,6-Tetrahydro-2,6-dioxo-4-pyrimidinecarboxamido)-cephalosporanic acid is obtained according to the process of Example 1 by reaction of 7-aminocephalosporanic acid with orotic acid chloride in a mixture of methylene chloride, tetrahydrofurane and acetone in the presence of triethylamine. The product is precipitated from methanol solution by means of a mixture of ether and petroleum ether. Melting point 195°–198° C. (decomposition). $[\alpha]_D^{20}=+161° \pm 1°$ (c=0.900 in dimethylsulphoxide). Thin layer chromatogram on silica gel: $Rf_{52A}=0.21$; $Rf_{67}=0.19$; $Rf_{101}=0.54$; $Rf_{101A}=0.45$.

EXAMPLE 12

10.0 g of the sodium salt of 3-benzoylthiomethyl-7-[D(−)-α-(1,2,3,4-tetrahydro-2,4-dioxo-5-pyrimidinecarboxamido)-phenylacetamido]-ceph-3-em-4-carboxylic acid are suspended in 60 ml of pyridine, 60 ml of dioxane and 40 ml of a 40% strength aqueous mercury perchlorate solution are then successively added to the suspension and the reaction mixture is vigorously stirred for 45 minutes at 45° C. in a nitrogen atmosphere. Thereafter the dark red solution is cooled to 0° C., 20 ml of thiobenzoic acid are added and the mixture is stirred for 5 minutes at +10° C. and extensively concentrated on a rotary evaporator (high vacuum) at 45° C. The residue is well mixed with 200 ml of water, the insoluble mercury salt is removed by filtering off through "Celite" and the filter residue is rinsed with 100 ml of water. The filtrate is successively extracted with 300 ml of toluene, three times with 200 ml at a time of a (1:1) mixture of "Amberlite" LA-2 and toluene and finally twice with 300 ml at a time of toluene. The aqueous phase is extensively concentrated on a rotary evaporator (high vacuum) at 45° C. and 7-[D(−)-α-(1,2,3,4-tetrahydro-2,4-dioxo-5-pyrimidinecarboxamido)-phenylacetamido]-3-(1-pyridylmethyl)-ceph-3-em-4-carboxylic acid betaine is precipitated by adding ethanol. 3.4 g of crude product are suspended in 20 ml of water and dissolved by adding 0.1 N sodium bicarbonate solution at pH 7.0. The solution is then cooled in an ice bath and adjusted to pH 4.5 with 1 N hydrochloric acid whilst stirring, whereupon the betaine precipitates. It is filtered off and washed with a little ice-cold water. Melting point 235°–240° C. (decomposition). Thin layer chromatogram on silica gel: $Rf_{52A}=0.10$; $Rf_{67}=0.03$; $Rf_{101}=0.35$; $Rf_{101A}=0.24$. $[\alpha]_D^{20}=-39° \pm 1°$ (c=0.961 in dimethylsulphoxide). UV spectrum in 0.5 N NaHCO$_3$: $\lambda_{max}=295$ nm ($\epsilon=15,000$); $\lambda_{max}=250$ nm ($\epsilon=14,200$); $\lambda_{min}=275$ nm ($\epsilon=14,150$). $ED_{50}=3$.

A part of the above betaine (4.0 g) is dissolved in 100 ml of water, 8.0 g of sodium iodide are added to the solution, the mixture is cooled in an ice bath and the pH is adjusted to 2.5 by dropwise addition of 2 N hydrochloric acid whilst stirring. The 7-[D(−)-α-(1,2,3,4-tetrahydro-2,4-dioxo-5-pyrimidinecarboxamido)-phenylacetamido]-3-(1-pyridylmethyl)ceph-3-em-4-carboxylic acid betaine hydrochloride obtained is filtered off and washed with a little cold water. Melting point 218°–220° C. (decomposition). $[\alpha]_D^{20}=-33° \pm 1°$ (c=0.859 in dimethylsulphoxide). UV spectrum: $\lambda_{max}$ 293 nm/$\epsilon=16,800$; $\lambda_{max}=238$ nm/$\epsilon=22,000$; $\lambda_{min}$ 272 nm/$\epsilon=14,700$ (in 0.5 N NaHCO$_3$). $ED_{50}=10$.

The starting material can be manufactured as follows:

A solution of 16.0 of the sodium salt of 7-[D(−)-(1,2,3,4-tetrahydro-2,4-dioxo-5-pyrimidinecarboxamido)-phenylacetamido]-cephalosporanic acid in 200 ml of water is added to a solution of 13.8 g of thiobenzoic acid and 8.4 g of sodium bicarbonate in 100 ml of water and the mixture is stirred for 20 hours at 50° C. in a nitrogen atmosphere. The viscous reaction mixture is then cooled to +5° C., covered with ethyl acetate and adjusted to pH 2.5 by adding 20% strength phosphoric acid, and the aqueous phase is repeatedly extracted with ethyl acetate. The extracts are combined, washed with sodium carbonate solution and dried over sodium sulphate, and the solvent is evaporated off on a rotary evaporator at 40° C. The oil which remains is mixed with a large amount of ether, whereupon solid 3-benzoylthiomethyl-7-[D(−)-α-(1,2,3,4-tetrahydro-2,4- dioxo-5-pyrimidinecarboxamido)-phenylacetamido]-ceph-3-em-4-carboxylic acid is obtained. Melting point 208°–210° C. (decomposition).

UV spectrum: $\lambda_{max}$ 290 nm/$\epsilon$=23,400; $\lambda_{max}$ 243 nm/$\epsilon$=21,400; $\lambda_{min}$ 260 nm/$\epsilon$=15,900 (in 0.5 N NaHCO$_3$). Thin layer chromatogram on silica gel: Rf$_{52A}$=0.48; Rf$_{67}$=0.32; Rf$_{101}$=0.59; Rf$_{101A}$=0.55.

EXAMPLE 13

7-[D(–)-$\alpha$-(1,2,3,6-Tetrahydro-2,6-dioxo-4-pyrimidinecarboxamido)-phenyl-acetamido]-3-(1-pyridylmethyl)-ceph-3-em-4-carboxylic acid betaine is obtained according to the process of Example 12 by reaction of 16.0 g of the sodium salt of 3-benzoylthiomethyl-7-[D(–)-$\alpha$-(1,2,3,6-tetrahydro-2,6-dioxo-4-pyrimidinecarboxamido)-phenylacetamido]-ceph-3-em-4-carboxylic acid with 64 ml of a 40% strength aqueous mercury perchlorate solution in a mixture of 96 ml of pyridine and 96 ml of dioxane. Melting point 285°–290° C. (decomposition). Thin layer chromatogram on silica gel: Rf$_{52A}$=0.05; Rf$_{101}$=0.34; Rf$_{101A}$=0.24. $[\alpha]_D^{20}$= –24°±1° (c=1.050 in dimethylsulphoxide). UV spectrum in 0.5 N NaHCO$_3$: $\lambda_{max}$=315 nm ($\epsilon$=6,500); $\lambda_{max}$=260 nm ($\epsilon$=11,900); $\lambda_{min}$=295 nm ($\epsilon$=6,000). ED$_{50}$=10.

7-[D(–)-$\alpha$-(1,2,3,6-Tetrahydro-2,6-dioxo-4-pyrimidinecarboxamido)-phenylacetamido]-3-(1-pyridylmethyl)-ceph-3-em-4-carboxylic acid betaine hydroiodide melts at 251°–253° C. with decomposition. UV spectrum: $\lambda_{max}$ 315 nm/$\epsilon$=7,650; $\lambda_{max}$ 260/$\epsilon$=16,000; $\lambda_{max}$240 nm/$\epsilon$=16,000; $\lambda_{min}$ 295 nm/$\epsilon$=6,600; $\lambda_{min}$ 250 nm/$\epsilon$=15,900 (in 0.5 N NaHCO$_3$).

The starting material can be manufactured as follows:

3-Benzoylthiomethyl-7-[D(–)-$\alpha$-(1,2,3,6-tetrahydro-2,6-dioxo-4-pyrimidinecarboxamido)-phenylacetamido]-ceph-3-em-4-carboxylic acid is obtained according to the process of Example 12 by reaction of a solution of 19.0 g of the sodium salt of 7-[D(–)-$\alpha$-(1,2,3,6-tetrahydro-2,6-dioxo-4-pyrimidinecarboxamido)-phenylacetamido]-cephalosporanic acid in 100 ml of water with a solution of 13.8 g of thiobenzoic acid and 8.4 g of sodium bicarbonate in 100 ml of water. Melting point 225°–229° C. (decomposition). UV spectrum: $\lambda_{max}$ 280 nm/$\epsilon$=15,700; $\lambda_{max}$ 248 nm/$\epsilon$=15,800; $\lambda_{min}$ 262 nm/$\epsilon$=15,300; $\lambda_{min}$ 315 nm/$\epsilon$=7,250 (in 0.5 N NaHCO$_3$). Thin layer chromatogram on silica gel: Rf$_{52A}$=0.51; Rf$_{67}$=0.35; Rf$_{101}$=0.61; Rf$_{101A}$=0.52.

EXAMPLE 14

6$\beta$-(1,2,3,4-Tetrahydro-2,4-dioxo-5-pyrimidinecarboxamido)-penicillanic acid is obtained according to the process of Example 1 by reaction of 6$\beta$-amino-penicillanic acid with uracil-5-carboxylic acid chloride in a mixture of methylene chloride, tetrahydrofurane and acetone in the presence of triethylamine. The product is recrystallised from methanol. Melting point 210°–212° C. (decomposition). $[\alpha]_D^{20}$= +107°±1° (c=1.113 in dimethylsulphoxide). Thin layer chromatogram on silica gel: Rf$_{52A}$=0.53; Rf$_{67}$=0.27; Rf$_{101}$=0.50; Rf$_{101A}$=0.44.

EXAMPLE 15

7-[D(–)-$\alpha$-(1,2,3,4-Tetrahydro-2,4-dioxo-5-pyrimidinecarboxamido)phenylacetamido]-3-[1-(4-carbamoylpyridiniomethyl)]-ceph-3-em-4-carboxylate is obtained according to the process of Example 12 by reaction of 5.5 g of the sodium salt of 3-benzoylthiomethyl-7-[D(–)-$\alpha$-(1,2,3,4-tetrahydro-2,4-dioxo-5-pyrimidinecarboxamido)-phenylacetamido]-ceph-3-em-4-carboxylic acid with 22.0 g of isonicotinic acid amide and 40 ml of a 40% strength aqueous mercury perchlorate solution in a mixture of 80 ml of dioxane and 20 ml of water. Purification of the crude product: 2.6 g of crude product are suspended in 20 ml of water and dissolved at pH 7.0 by adding 0.1 N sodium bicarbonate solution, and the solution is cooled in an ice bath and adjusted to pH 3.0 with 1 N hydrochloric acid whilst stirring, whereupon the betaine precipitates. It is filtered off and washed with a little ice-cold water. Melting point 198°–200° C. decomposition). $[\alpha]_D^{20}$= –45°±1° (c=1.035 in dimethylsulphoxide). Thin layer chromatogram on silica gel: Rf$_{52A}$:0.13; Rf$_{67}$=0.10; Rf$_{101}$=0.38; Rf$_{101A}$=0.42. UV spectrum in 0.5 N NaHCO$_3$: $\lambda_{max}$=290 nm ($\epsilon$=16,500) and $\lambda_{flat}$=250–260 nm ($\epsilon$=15,500).

The following compounds can be obtained analogously: 7-[D(–)-$\alpha$-(1,2,3,4-Tetrahydro-2,4-dioxo-5-pyrimidinecarboxamido)-phenylacetamido]-3-[1-(4-methylpyrimidinomethyl)]-ceph-3-em-4-carboxylate by reaction of the sodium salt of 3-benzoylthiomethyl-7-[D(–)-$\alpha$-(1,2,3,4-tetrahydro-2,4-dioxo-5-pyrimidinecarboxamido)-phenylacetamido]-ceph-3-em-4-carboxylic acid with 4-methylpyridine; 7-[D(–)-$\alpha$-(1,2,3,4-tetrahydro-2,4-dioxo-5-pyrimidinecarboxamido)-phenylacetamido]-3-[1-4-ethylpyridiniomethyl)]-ceph-3-em-4-carboxylate by reaction of the same starting material with 4-ethylpyridine; 7-[D(–)-$\alpha$-(1,2,3,4-tetrahydro-2,4-dioxo-5-pyrimidinecarboxamido)-phenylacetamido]-3-[1-(4-chloropyridininomethyl]-ceph-3-em-4-carboxylate by reaction of the same starting material with 4-chloropyridine; 7-[D(–)-$\alpha$-(1,2,3,4-tetrahydro-2,4-dioxo-5-pyrimidinecarboxamido)-phenylacetamido]-3-[1-(4-carboxypyridiniomethyl)]-ceph-3-em-4-carboxylate by reaction of the same starting material with isonicotinic acid; 7-[D(–)-$\alpha$-(1,2,3,4-tetrahydro-2,4-dioxo-5-pyrimidinecarboxamido)-phenylacetamido]-3-[1-(3-hydroxypyridiniomethyl)]-ceph-3-em-4-carboxylate by reaction of the same starting material with 3-hydroxypyridine.

EXAMPLE 16:

2.72 g of 7-amino-cephalosporanic acid are suspended in 30 ml of a (1:1) mixture of methylene chloride and tetrahydrofurane and 2.10 ml of triethylamine are added at room temperature whilst stirring, whereupon a clear brown solution is produced. The solution is then cooled to 0° C. in an ice bath, a solution of 2.30 g of D(–)-$\alpha$-(2,4-dioxo-1,2,3,4-tetrahydro-5-pyrimidinecarboxamido)-phenylacetyl chloride (manufactured by reaction of D(–)-$\alpha$-(2,4-dioxo-1,2,3,4-tetrahydro-5-pyrimidinecarboxamido)-phenylacetic acid with thionyl chloride in tetrahydrofuran) in 70 ml of tetrahydrofurane is added dropwise over the course of 20 minutes at 0° C. to +5° C., whilst stirring and cooling in an ice-bath, and the mixture is then stirred for 90 minutes at 0° C. 70 ml of phosphate buffer solution of pH 7.5 are then added to the reaction mixture, which is worked up as in Example 1. The product is identical with 7-[D(–)-$\alpha$-(2,4-dioxo-1,2,3,4-tetrahydro-5-pyrimidinecarboxamido)-phenylacetamido]-cephalosporanic acid obtained according to the process of Example 9.

We claim:

1. A compound of the formula I

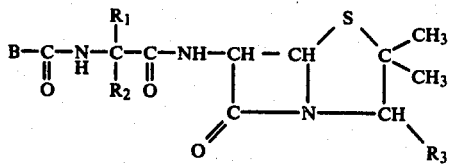

wherein R₃ denotes a free or conventional penicillin therapeutically useable esterified carboxyl group, and wherein, if the radicals R₁ and R₂ are separate, R₁ is hydrogen and R₂ is phenyl, thienyl, furyl, or phenyl, which is substituted by lower alkyl with up to 6 carbon atoms, lower alkoxy with up to 4 carbon atoms, halogen, trifluoromethyl, nitro, carbamoyl, or lower alkanoyl with up to 6 carbon atoms, and, if the radicals R₁ and R₂ are linked, they form, together with carbon atoms, a cycloalkyl with up to 7 carbon atoms, and wherein B represents 1,2,3,6-tetrahydro-2,6-dioxo-pyrimidyl, a 2,6-dichloropyrimidyl or 2,6-dimethoxypyrimidyl, in which the pyrimidyl groups are bonded in 4- or 5-position of the ring at a carbon atom and are unsubstituted or substituted at a carbon atom by halogen, lower alkyl with up to 4 carbon atoms or phenyl, and conventional therapeutically useable salts thereof with the proviso that if R₁ is hydrogen, R₂ is phenyl and R₃ is carboxyl, B does not represent an unsubstituted 1.2.3.6-tetrahydro-2.6-dioxo-pyrimidyl radical, which is bonded in 5-position.

2. The compound of formula I as claimed in claim 1, wherein R₃ denotes carboxyl, R₁ represents hydrogen, R₂ represents phenyl, thienyl(2) or furyl(2) and B has the meaning indicated in claim 1, and conventional therapeutically usable salts thereof.

3. The compound of formula I as claimed in claim 1, wherein R₁ represents hydrogen, R₂ represents phenyl, R₃ denotes carboxyl and B has the meaning indicated in claim 1, and conventional therapeutically usable salts thereof.

4. The compound of formula I as claimed in claim 1, wherein R₃ is carboxyl, R₁ represents hydrogen and R₂ represents phenyl and B denotes a 1,2,3,6-tetrahydro-2,6-dioxopyrimidyl(4)-radical or said radical substituted by lower alkyl, halogen or phenyl, and conventional therapeutically usable salts thereof.

5. A compound as claimed in claim 1, which is 6-[D(−)-α-1,2,3,6-tetrahydro-2,6-dioxo-4-pyrimidine-carboxamido)-phenylacetamido]-penicillanic acid or an enzymetically splittable ester or a conventional therapeutically useable salt of this compound.

6. A pharmaceutical preparation for combating infections caused by gram-positive or gram-negative bacteria which comprises a therapeutically effective amount of a compound of formula I of claim 1 in the presence of a pharmaceutically usable excipient.

* * * * *